United States Patent [19]

Peik et al.

[11] 4,401,760
[45] Aug. 30, 1983

[54] HETEROPOLYSACCHARIDE S-194

[75] Inventors: Jerry A. Peik, San Diego; Suzanna M. Steenbergen, Lakeside; Harold R. Hayden, Escondido, all of Calif.

[73] Assignee: Merck & Co., Inc., Rahway, N.J.

[21] Appl. No.: 313,440

[22] Filed: Oct. 21, 1981

[51] Int. Cl.$^3$ .......... C12P 19/04; C12N 1/20; C12R 1/05
[52] U.S. Cl. .......... 435/101; 435/253; 435/829; 536/123
[58] Field of Search .......... 435/253, 829, 101

[56] References Cited

U.S. PATENT DOCUMENTS 3,822,250  7/1974  Kimura et al. .......... 435/829 X
3,856,626  12/1974  Clamen et al. .......... 435/829 X

FOREIGN PATENT DOCUMENTS 56-109593  8/1981  Japan .......... 435/829
56-121496  9/1981  Japan .......... 435/829
2058107  8/1981  United Kingdom .......... 435/101

Primary Examiner—Lionel M. Shapiro
Attorney, Agent, or Firm—Gabriel Lopez; Hesna J. Pfeiffer

[57]  ABSTRACT

A novel polysaccharide S-194 is disclosed composed of principally carbohydrate, about 14% protein, and 9-11% O-acetyl groups. The carbohydrate portion comprises about 8.8-9.2% glucuronic acid and the neutral sugars glucose and rhamnose in the approximate molar ratio 4:1. This polysaccharide is produced by a new Alcaligenes species ATCC 31961, in a suitable fermentation medium.

7 Claims, No Drawings

HETEROPOLYSACCHARIDE S-194

BACKGROUND OF THE INVENTION

It is known that heteropolysaccharides can be produced by certain microorganisms. Some of these heteropolysaccharides function as hydrophilic colloids and because of their viscosity and rheology properties have been used as thickening agents for aqueous systems.

As with other fields of technology, research has continued with the objective of discovering new heteropolysaccharides having useful properties as thickening, suspending and/or stabilizing agents. It is an object of this invention to provide a new heteropolysaccharide, which is produced from a new Alcaligenes strain. It is another object to provide a method for making this new compound. A still further object is provision of formulations containing the new heteropolysaccharide as a thickening or suspending or stabilizing agent. Other objects of the invention will become evident from the ensuing description of this invention.

SUMMARY OF THE INVENTION

The present invention pertains to a novel heteropolysaccharide which is produced by the action of a bacterium on a selected carbon source. Further, the invention pertains to a novel process for producing the heteropolysaccharide by bacterial fermentation of a selected carbon source and fermentation medium ingredients under controlled conditions. The heteropolysaccharide of this invention is a high molecular weight polysaccharide containing primarily carbohydrate. It is sometimes referred to as a "gum" but it is believed that the heteropolysaccharide terminology is more accurate and precise. In the following description of the invention, it will sometimes be referred to as Heteropolysaccharide S-194 or simply S-194.

This novel compound may be prepared in recoverable amounts by fermentation of a suitable nutrient medium with an organism, an Alcaligenes species. An unrestricted permanent deposit of an organism of this species employed in making the heteropolysaccharide was made with the American Type Culture Collection on Sept. 17, 1981 under Accession No. ATCC 31961.

The organism was isolated from a pool in the Glacier Basin area in the Rocky Mountains near Denver, Colo. The organism was picked as a gummy colony after four days' incubation at 30° C. from a YM (Difco) agar plate. The isolate was then pure cultured on nutrient agar.

Taxonomic studies of ATCC 31961 indicate that it does not correspond to any of the Alcaligenes species in Bergey's Manual.

A YM flask seed was started with a fresh NA plate and placed on a gyratory shaker at 30° C. Approximately 24 hrs. later this seed was used to inoculate an E-1 flask with 3% hydrolyzed starch as the carbon source. This flask was also placed on a shaker at 30° C. Approximately 72 hrs. later the flask was noted to have viscous beer and upon addition of two volumes of 99% IPA a fibrous precipitate was observed.

Another YM seed flask was prepared in the above fashion and used at 24 hrs. to inoculate five flasks containing various media and 3% glucose. These flasks were incubated on a shaker at 30° C. for about 72 hrs. at which time the pH, viscosity, gum yield, and product viscosity were measured. The results are shown in Table 1.

E-1 medium contains 5 gms of dipotassium phosphate, 0.1 gm of magnesium sulfate, 0.9 gm of ammonium nitrate, 0.5 gm of Promosoy 100 (an enzymatic digest of soybean meal sold by Central Soya Chemurgy Division), 30 gms of dextrose and 1 liter of tap water. The pH of the E-1 medium is about 7.6 to 7.8.

TABLE 1
EFFECT OF MEDIA ON GUM PRODUCTION

| Medium | pH | Beer Vis. (cP) | Gum Yield (%) | 1% Product Vis. (cP) |
|---|---|---|---|---|
| E-1 | 6.3 | 1300 | 0.882 | ND |
| E-1 − NH$_4$NO$_3$ + 0.19% NaNO$_3$ | 7.0 | 600 | 0.520 | ND |
| E-1 + 0.20% Promosoy | 5.9 | 3800 | 1.482 | 1550 |
| E-1 + HoLe$^2$ salts | 6.2 | 1800 | 0.790 | 1200 |

$^1$ND: Not determined
$^2$HoLe salts: An aqueous solution comprising:

| | Conc. In Final Medium (ppm) |
|---|---|
| H$_3$BO$_3$ | 0.05 B$^{+3}$ |
| MnCl$_2$.4H$_2$O | 0.5 Mn$^{+2}$ |
| FeSO$_4$ | 0.5 Fe$^{+2}$ |
| Na$_2$C$_4$H$_4$O$_6$.2HO (Na Tartrate) | |
| CuCl$_2$ | 0.01 Cu$^{+2}$ |
| ZnCl$_2$ | 0.02 Zn$^{+2}$ |
| CoCl$_2$.6H$_2$O | 0.01 Co$^{+2}$ |
| Na$_2$MoO$_4$.2H$_2$O | 0.01 Mo$^{+6}$ |

S-194 prepared in shaker flasks has exhibited the following profile of properties. The data are obtained at room temperature.

1. VISCOSITY AND SHEAR

| A. Brookfield LVF visc. | D.I. H$_2$O | Tap H$_2$O | Tap H$_2$O + 0.1% KCl |
|---|---|---|---|
| 1. 1.0% @ 60 rpm, spin. 3 | | 1660 cP | 1820 cP |
| @ 6 rpm, spin. 3 | | 11,800 cP | |
| 2. 0.1% No. 1 spin & UL adapter @ 6 rpm | | 32 cP | 34.5 cP |
| 3. 0.5% Wells-Brookfield attachment, @ 9.6 sec$^{-1}$ | | 530 cP | 614 cP |
| 4. 1.0% @ 60 rpm, spin. 3 | 1650 cP | | |

2. SALT AND DYE COMPATIBILITY

| A. Salt | | |
|---|---|---|
| 1. CaCl$_2$ (Saturated) | Compatible* | |
| 2. Amm. polyphosphate | Compatible* | |
| 3. 60% NH$_4$NO$_3$ | Compatible* | |
| 4. 1% Al$_2$(SO$_4$)$_3$.18H$_2$O | Compatible* | |
| 5. 1% CaCl$_2$.2H$_2$O | Compatible* | |
| 6. 1% KCl | Compatible* | |
| B. Dyes | | |
| 1. Milling Green | Compatible | |
| 2. Methylene Blue | Precipitate | (indicating S-194 has a net negative charge) |

| C. Visc. in Ammonium polyphosphate: | | |
|---|---|---|
| Initial | 24 Hrs. | % Change |
| 910 cP | 720 cP | −20 |

*The resultant solutions were observed for either precipitation or gelation; neither was observed.

3. TEXTURE/FLOW PROPERTIES

Smooth, continuous flow; no gelation; gummy to the touch.

4. WORKING YIELD VALUE 62 dynes/cm$^2$, 1% solution in S.T.W.*

*Standard tap water is 0.01% $CaCl_2$ and 0.1% NaCl in DI water.

FERMENTATION CONDITIONS

Heteropolysaccharide S-194 is produced during the aerobic fermentation of suitable aqueous nutrient media under controlled conditions via inoculation with the organism ATCC 31961. The media contain a source of carbon, nitrogen, and inorganic salts.

In general, carbohydrates (for example, glucose, fructose, maltose, sucrose, xylose, mannitol and the like) can be used either alone or in combination as sources of assimilable carbon in the nutrient medium. The exact quantity of the carbohydrate source or sources utilized in the medium depends in part upon the other ingredients of the medium but, in general, the amount of carbohydrate usually varies between about 2% and 5% by weight of the medium. These carbon sources may be combined in the medium. In general, many proteinaceous materials may be used as nitrogen sources in the fermentation process. Suitable nitrogen sources include, for example, yeast hydrolysates, primary yeast, soybean meal, cottonseed flour, hydrolysates of casein, cornsteep liquor, distiller's solubles or tomato paste and the like. The sources of nitrogen, either alone or in combination, are used in amounts preferably ranging from about 0.05% to 0.2% by weight of the aqueous medium. Promosoy 100 can be used in the range 0.005 to 0.4%.

Among the nutrient inorganic salts which can be incorporated in the culture media are the customary salts capable of yielding sodium, potassium, ammonium, calcium, phosphate, sulfate, chloride, carbonate, and the like ions. Also included are trace metals such as cobalt, manganese, iron and magnesium.

It should be noted that the media described in the examples are merely illustrative of the wide variety of media which may be employed, and are not intended to be limiting.

As an alternate medium, S-194 may be grown under low $Ca^{++}$ conditions, i.e., in deionized water or some other aqueous system substantially free of $Ca^{++}$ ions (i.e., less than about 4 ppm $Ca^{++}$ per 1% gum in the final fermentor broth).

The fermentation is carried out at temperatures ranging from about 25° C. to 35° C.; however, for optimum results it is preferable to conduct the fermentation at temperatures of from about 28° C. to 32° C. The pH of the nutrient media for growing the ATCC 31961 culture and producing the polysaccharide S-194 can vary from about 6 to 8.

Although the polysaccharide S-194 is produced by both surface and submerged culture, it is preferred to carry out the fermentation in the submerged state.

A small scale fermentation is conveniently carried out by inoculating a suitable nutrient medium with the culture and, after transfer to a production medium, permitting the fermentation to proceed at a constant temperature of about 30° C. on a shaker for several days.

The fermentation is initiated in a sterilized flask of medium via one or more stages of seed development. The nutrient medium for the seed stage may be any suitable combination of carbon and nitrogen sources.

The seed flask is shaken in a constant temperature chamber at about 30° C. for 1-2 days, or until growth is satisfactory, and some of the resulting growth is used to inoculate either a second stage seed or the production medium. Intermediate stage seed flasks, when used, are developed in essentially the same manner; that is, part of the contents of the flask from the last seed stage are used to inoculate the production medium. The inoculated flasks are shaken at a constant temperature for several days, and at the end of the incubation period the contents of the flasks are recovered by precipitation with 2-3 volumes of a uitable alcohol such as isopropanol, or with the alco hol in the form of CBM (an 85:15 alcohol:-water constant boiling mixture).

For large scale work, it is preferable to conduct the fermentation in suitable tanks provided with an agitator and a means of aerating the fermentation medium. According to this method, the nutrient medium is made up in the tank and sterilized by heating at temperatures of up to about 121° C. Upon cooling, the sterilized medium is inoculated with a previously grown seed of the producing culture, and the fermentation is permitted to proceed for a period of time as, for example, from 2 to 4 days while agitating and/or aerating the nutrient medium and maintaining the temperature at about 30° C. This method of producing the S-194 is particularly suited for the preparation of large quantities.

Although ATCC 31961 can be grown under a broad spectrum of media conditions, the following preferred conditions are recommended.

1. CULTURE MAINTENANCE

This culture must be maintained on YM agar. Nutrient agar should not be used. A variant has been observed which does not produce polysaccharide. This variant is indistinguishable from the wild type on NA. However, it is readily discernable on YM agar.

On YM agar, the colonies reach a size of 1.5-2 mm after three days incubation. Typical wild type colonies are yellow, round, entire, convex, opaque, and glistening. The colonies are hard and rubbery. The variant colonies are raised (but not convex) and soft or mucoid rather than hard.

The culture should be transferred every three to four days. In doing so, single colonies should be picked for restreaking rather than the dense area of growth.

2. SEED PREPARATION

Fresh YM agar plates (48-72 hrs) are used to start either YM or YN+0.25% $K_2HPO_4$ flasks. These flasks are incubated with shaking at 30° C. and transferred (1-5% inoculum) to fresh YM or YM+0.25% $K_2HPO_4$ flasks at 24 hrs. After shaking at 30° C. for 24-30 hrs., two of these flasks are used to inoculate a one-gallon fermentor containing 3 L of the following seed medium.

3.0% Glucose
0.5% $K_2HPO_4$
0.2% Promosoy 100
0.01% $MgSO_4.7H_2O$
0.09% $NH_4NO_3$
0.1-0.05% Antifoam An inoculum size of 5-10% is used at 24-30 hours to inoculate the final fermentor. This fermentation is compatible with the following antifoams.

0.01% K-60/Balab
0.05% SAG 471
0.05% FCA 200
0.05% DOW C
0.10% Proflo Oil

3. 70 L FERMENTOR MEDIUM

The final fermentor medium is the same as the seed medium except that the phosphate level is lower:

3.0% Glucose
0.05% $K_2HPO_4$
0.20% Promosoy 100
0.01% $MgSO_4.7H_2O$
0.09% $NH_4NO_3$
0.01–0.05% Antifoam The pH is controlled at 6.5–7.0 with 35% KOH. The fermentation is run at 30° C. Fermentation times range from 60–72 hrs with beer viscosities ranging from 3400–4900 cP, measured on a Brookfield LVF viscometer, spindle No. 4, 60 rpm, at room temperature. Conversion efficiencies vary from 44–59% with 3% glucose.

Flask results have shown that $Na_2HPO_4$ cannot be substituted. The organism is either very sensitive to sodium or else has a definite requirement for potassium. Recent flask work has also indicated that higher levels of Promosoy 100, i.e. 0.4%, can result in greater gum yields.

4. RECOVERY

On completion of the fermentation, the heteropolysaccharide S-194 may be recovered by treatment of the fermentation beer with a miscible solvent which is a poor solvent for the heteropolysaccharide and does not react with it. In this way the heteropolysaccharide is precipitated from solution. The quantity of solvent employed generally ranges from about 2 to about 3 volumes per volume of fermentation beer. Among the various solvents which may be employed are acetone and lower alkanols such as methanol, ethanol, isopropanol, n-butanol, sec-butanol, tertiary butanol, isobutanol, and n-amyl alcohol. Isopropanol is preferred. The pH of the final beer should be adjusted to 6.5–6.8 with $H_2SO_4$ prior to recovery. Typically, the fermentation beer is heated to a temperature of about 75° C. for a short time (e.g., about 10 to 15 minutes), and then cooled to about 30° C. or lower before addition of the solvent. A spent alcohol concentration of 55–56% is required for precipitating the heteropolysaccharide from the fermentation beer. The solid is recovered by separating it from the liquid, as by filtering or straining, and then drying at elevated temperature.

5. DRYING

The product is dried at 55° C. for up to one hour in a forced-air tray drier.

HETEROPOLYSACCHARIDE S-194

The heteropolysaccharide produced by ATCC 31961 is composed of principally carbohydrate, about 10% O-acetyl groups, substantially no pyruvate, and about 10% protein.

The carbohydrate portion of the S-194 polysaccharide contains about 9% glucuronic acid (based on wt. gum) and the neutral sugars glucose and rhamnose in the approximate molar ratio of 4:1.

Colloidal titration (DIMDAC/sulphonic acid method) and potentiometric titration both indicate the gum is acidic (0.5–0.7 mequiv. of anionic groups/gm gum). An acetyl content of 9–11% was determined by treating a 0.2% aqueous solution of S-194 gum with an alkaline, hydroxylamine reagent followed by treatment with an acidic ferric chloride reagent [S. Hestrin (1949) *J. Biol. Chem.* 180 249–261].

20 mg of S-194 were hydrolyzed in 1 ml of 2 N $H_2SO_4$ at 100° C. for four hours. After cooling, 0.5 ml of 3 mg/ml xylose was added as an internal standard. Samples were neutralized by adding 3 ml of saturated Ba(OH)$_2$, then 2 drops of Congo Red and Ba(OH)$_2$ until the color changed to red. Solid $CO_2$ was added to neutralize excess hydroxyl ions. After centrifuging (30 min, 2000 rpm) the supernatants of all samples were evaporated. Dry samples were derivatized in 0.1 ml hydroxylamine HCl (40 mg/ml in dry pyridine) and heated at 90° C. for 45 minutes. To the cooled samples, 0.1 ml of redistilled acetic anhydride was added and the samples heated to 90° C. for 45 minutes. The sugars were separated by gas-liquid chromatography of their aldononitrile acetate derivatives on a 6'×2 mm I.D. glass column, 3% SP-2330, on 100/120 mesh Supelcoport. The sugars were identified and quantitated by comparison with authentic standards [J. K. Baird, M. J. Holroyde, and D. C. Ellwood (1973) Carbohydr. Res. 27 464–467]. See Table 2 for determination of the neutral sugars.

TABLE 2

| Total Neutral Sugars in S-194 | |
|---|---|
| Sugar | Wt. % |
| Rhamnose | 20–21 |
| Glucose | 73–77 |
| Mannose | |
| Ribose, and | |
| Arabinose | trace amounts, <5% total |

The various neutral sugars of the polysaccharides were also characterized by use of descending paper chromtography on Whatman No. 1 chromatography paper using as the solvent the upper layer of pyridine-:ethyl acetate:water (2:5:5). chromatograms were stained using a silver nitrate dip reagent and acid aniline phthalate spray reagent. Component sugars were identified by co-chromatography with sugar standards and by the specific-color reaction with the aniline phthalate reagent.

The glucuronic acid content of the polysaccharide was determined by decarboxylation with 17% hydrochloric acid, followed by trapping the liberated carbon dioxide in standard sodium hydroxide and back titration [B. L. Browning (1967) *Methods of Wood Chemistry II*, 632–633]. The decarboxylation method gave the values 8.8, 8.9, and 9.2% for three different samples of S-194.

Paper electrophoresis was used for the separation and tentative identification of the uronic acids present in the neutralized acid hydrolysate described above. Aliquots of this and known uronic acid standards were applied to Camag electrophoresis paper No. 68-011 and electrophoresis was carried out for 2.0 hours in a pH 2.7 buffer using a Camag Model HVE electrophoresis apparatus. Chromatograms were air dried and stained with silver nitrate dip reagent to locate the uronic acids being separated. Two uronic acid spots were found by this method which had the relative mobilities of glucuronic acid and mannuronic acid standards, the latter spot representing an acid resistant uronic acid-containing disaccharide.

An infrared spectrum of native S-194 was made on dried material in a KBr pellet. The heteropolysaccharide evidenced peaks at: 3400 cm$^{-1}$, 2920 cm$^{-1}$, and 1725 cm$^{-1}$ indicating hydroxyl, methyl, and ester groups, respectively.

Sample of S-194 were dialyzed and freeze dried after fermentation. The samples were methylated according to the procedures outlined in Sandford and Conrad, Biochemistry 5 (1966) 1508–1517.

The methyl ether derivatives of the sugars as their aditol acetates were separated by gas chromatography. The relative amounts of the O-methyl derivatives of glucose and rhamnose are given in Table 3.

TABLE 3

Relative Amounts of O—Methyl Sugars in a Hydrolysate of Methylated S-194

| Methyl Sugars | Linkage | Approx. Molar Ratio |
|---|---|---|
| 2,3 Me$_2$ Rhamnose | 1,4 | 1 |
| 2,3,4,6 Me$_4$ Glucose | Terminal | 1 |
| 2,3,4 Me$_3$ Glucose | 1,6 | 1 |
| 2,3,6 Me$_3$ Glucose | 1,4 | 1 |
| 2,4 Me$_2$ Glucose | 1,3,6 | 1 |

S-194 is, therefore, most likely composed of a six member repeating unit composed of equimolar amounts of the five sugars of Table 3 and glucuronic acid which is most likely not terminally linked.

Heteropolysaccharide S-194, as determined on four different samples, has the following profile of properties:

TABLE 4

SOLUTION PROPERTIES OF S-194

| Test | BD 867 | BD 1103 | BD 1104 | BD 1105 |
|---|---|---|---|---|
| 1% Visc./ STW (cP) | 730 | 900 | 1120 | 1190 |
| WYV (dynes/cm$^2$) | 36.0 | 37 | 48 | 50 |
| pH stability | 2–12 | 2–12 | 2–12 | 2–12 |
| Heat stability % visc. recovery Fann 50 (STW) | 436% | 318% | 219% | 283% |
| Shear stability Waring Blender, 15 min., % visc. change | +67% | +20% | +59% | +77% |
| Brine Visc. (cP) Fann 35, 3 rpm: | | | | |
| a. Seawater | 319.3 | — | — | — |
| b. Sat. CaCl$_2$.2H$_2$O | 30.9 | — | — | — |
| c. Permian Brine | 618.0 | — | — | — |
| d. Standard Brine | 350.2 | — | — | — |

The polysaccharide S-194 imparts viscosity to aqueous media when dissolved in water in low concentrations. It is useful as a thickening, suspending, emulsifying, stabilizing, lubricating, film-forming, or binding agent, especially in aqueous systems. S-194 has a high viscosity and working yield value (WYV), excellent stability to heat, shear, and enzymes. It has good viscosity in brine and a constant viscosity over a pH range of 2.0–12.0. It also has fairly good thickening efficiency in hot ammonium nitrate formulations. Aqueous solutions of S-194 combined with guar, hydroxypropyl guar, or hydroxyethylcellulose exhibit synergistic viscosity increases, compared to solutions of each gum itself. In particular, it has uses in the following applications or products: adhesives, wall-joining cements, spackling compounds, can sealing, boiler compounds, latex creaming, welding-rod fluxes, brazing pastes, ceramic glazes and extrusions, cleaners and polishes, emulsions (latex, asphalt, silicone), silver recovery, seed coatings, spray control for pesticides or herbicides, flowable pesticides and herbicides, tobacco binders, water-based inks, stable foams, leather finishes, textile printing and finishing, wet-end paper additives, wet-end paper retention and formation aid, anti-stick compounds, mold-release agents, liquid resins, slurry and packaged explosives, petroleum and water-well drilling muds, petroleum workover and completion fluids, petroleum stimulation fluids, cosmetics, pharmaceutical suspensions and emulsions.

Also this gum has utility in food systems such as jellies and other high sugar systems, beverages including citric acid based drinks, dairy products including ice cream and yogurt, salad dressings, dry mixes, icings, ang glazes, syrups, puddings, farinaceous foods, canned and retorted foods, and bakery fillings.

A primary application for S-194 is in suspension fertilizers. The materials used to produce suspensions are common to all types of fertilizers, containing various ratios of nitrogen, phosphate and potassium. Nitrogenous materials include ammonia, ammonium salts, urea, and urea/ammonium nitrate solution blends commonly called UAN solutions. Phosphate sources include phosphoric acid and ammonium phosphates which also serve as a source of nitrogen. The most commonly used salts are liquid ammonium polyphosphate solutions such as 10-34-0 and 11-37-0, although other grades are available. In recent years ammonium orthophosphates such as monoammonium phosphate (MAP) and diammonium phosphate (DAP) have gained increased acceptance due to availability. Special combinations such as urea/ammonium polyphosphate, 28-28-0, are also used. Potassium sources are predominantly impure grades of potassium chloride, although the sulfate and nitrate salts are also used.

The only suspension stabilizer commercially used to date has been clay, (attapulgite or bentonite). Clays have several disadvantages: viscosity is often affected by UAN solutions, high shear mixing is necessary to fully hydrate and swell the clay particles, and severe dust problems often arise from the large amounts used. Clays may also inactivate some pesticides which adsorb on the clay surfaces. Common gums and thickeners such as guar, cellulose derivatives, and xanthan gum are usually incompatible with the high concentrations of ammonium polyphosphate or orthophosphates.

Polysaccharide S-194 is compatible with a wide variety of ammonium phosphate salts, has the proper rheology to produce good suspensions, does not inactivate pesticides by absorption, and the small amount used alleviates dusting problems associated with clay.

The use of S-194 in suspension fertilizers involves first the preparation of a solution of S-194 in the available water or water/UAN combinations, then addition of the ammonium phosphates followed by the potassium chloride. S-194 also dissolves directly in urea/ammonium nitrate solutions such as 28-0-0 or 32-0-0. In preparing some mixed grade products, uran solutions are often mixed with base suspensions which already contain clay which is then diluted by the nitrogen solution. This results in insufficient clay to suspend the salts. The use of UAN solutions made viscous with S-194 helps prevent viscosity loss in clay systems as well.

The use level of S-194 in suspension fertilizers is 0.5 to 5.0 pounds/ton, preferably 1.0 to 3.0 pounds/ton (0.05–0.15%). For preparation of viscous urea/ammonium nitrate solutions, a preferred range is 0.15% to 0.5% by weight although 0.05% to 1.0% by weight can be used.

S-194 is particularly effective in suspensions of flowable pesticides due to its high viscosity at low concentrations and low shear rates and its excellent shear stability. During the production of flowables it is common practice to grind the pesticide to a small particle size in order to produce a more effective product and a more stable suspension, ball mills, sand mills and attriters are used to grind the particles and produce a high shear during the process. In order to avoid shear degradation of the thickener it is common practice to add the thickener near the end of the milling process. S-194 is so shear stable that it may be added at the beginning thus saving valuable processing time.

The invention is further defined by reference to the following examples, which are intended to be illustrative and not limiting.

EXAMPLE 1

Preparation of S-194

The initial seed flask containing 100 ml of YM broth was inoculated with a loopful of a culture (Alcaligenes species, ATCC 31961) from a fresh NA plate. After incubation for 24 hrs at 30° C. with shaking, a 1% transfer was made to fresh YM flasks. After a similar incubation period two of these flasks were used to inoculate a five-liter fermentor containing three liters of the following medium:

3.0% Glucose
0.50% $K_2HPO_4$
0.20% Promosoy 100
0.01% $MgSO_4.7H_2O$
0.09% $NH_4NO_3$
0.07% SAG 471 antifoam The temperature was maintained at 30° C. and the aeration at one liter per minute. The agitation was started at 400 RPM and increased thereafter to ensure good mixing. At 24 hrs approximately 2.5 liters of this seed were used to inoculate a 30 L fermentor containing 20 liters of the following medium:

3.0% Glucose
0.05% $K_2HPO_4$
0.20% Promosoy 100
0.01% $MgSO_4.7H_2O$
0.09% $NH_4NO_3$
0.05% SAG 471 antifoam The temperature was maintained at 30° C. and the aeration rate at 10 liters per minute throughout the fermentation. The pH was automatically controlled at above 6.7 by the addition of 25% KOH. The agitation was initially set at 300 RPM and was increased to a maximum of 700 RPM as needed to ensure good mixing. The results of this fermentation are given below.

| Age    | pH   | Beer Visc.* | Gum Yield | Residual Carbon Source |
|--------|------|-------------|-----------|------------------------|
| 66 hrs | 6.75 | 1200 cPs    | 0.84%     | 1.0%                   |
| 89 hrs | 7.44 | 2300 cPs    | 1.28%     | 0.1%                   |

*Brookfield VLF, spin. No. 4, 60 rpm.

The fermentation liquor was then heated to approximately 75° C. for 10–15 minutes and then cooled to ambient temperature. The fermentation liquor was then added to three volumes of 99% isopropanol. The polysaccharide precipitated as fibrous material which was recovered with a sieve. After drying in a forced air tray drier at 55° C. for approximately 45 minutes the fibers were milled to a powder, identified as BD 947, heteropolysaccharide S-194.

EXAMPLE 2

S-194 Taxonomy

A. Morphological Observations

1. Colonial Morphology

On nutrient agar, very small colonies appeared after one day's incubation and the diameter of the colonies reached approximately 1 mm after three days' incubation. The colony was yellow pigmented (non-diffusible) round, entire convex, opaque and glistening. No rubbery texture was observed.

On YM agar, small colonies appeared in one day and their diameter reached 1.5–2.0 mm after three days' incubation. The colony was yellow pigmented (non-diffusible), round, entire convex, opaque and glistening. The texture of the colony became very rubbery and entire colonies were often removed when they were pushed by inoculation needles. Concentric rings appeared after prolonged incubation.

2. Cellular Morphology

The strain was a Gram-negative, rod shaped bacterium, motile by mixed flagellation, i.e., cells were monopolarly as well as peritrichously flagellated. Capsule, spore, and acumulation of poly-$\beta$-hydroxybutyrate granules (PHB) were not observed. Acid fast stain was negative.

On nutrient agar, the size of the cell was 0.5–0.6 by 1.5–2.0 $\mu$m, the cell was straight with tapered ends.

On YM agar, the cells were larger than those grown on nutrient agar. The size of the cell was 0.5–0.6 by 2.0–4.0 $\mu$m, the majority of the cells were straight, and more round ended. Some were curved. The cells were often observed in palisade arrangement in heavy gelatinous matrix which was very refractile under phase contrast microscopy. Volutin-like materials were often seen.

3. Growth in broth culture

Growth of the strain was limited only on the surface. Pellicle was formed in both nutrient and YM broth test tube cultures. An especially thick pellicle was observed in YM broth.

B. Physiological and Biochemical Tests

The following is a summary of results of physiological and biochemical tests employed which are listed in Table 2-1. Both cytochrome oxidase and catalase were positive. The organisms utilize glucose oxidatively, but not fermentatively. No anaerobic growth was observed. The organisms could grow at temperatures between 4° to 37° C., but not at 40° C. No survival was observed after incubation at 60° C. for 30 minutes. Maximum concentration of NaCl for tolerance was 1.5%. The organisms grew at both pH's 6 and 8, but not at pH's 4 and 10.

On TSI agar, growth was observed on the slant, but neither acid nor alkali reaction was observed, and no growth in the butt was seen. Almost all standard bacteriological tests were negative. No nitrate or nitrite was reduced. In litmus milk, no change was observed. The organism hydrolyzed starch, gelatin (weakly), esculin, Tween 80, but not casein and pectin.

The organisms produced acid oxidatively from L-arabinose, fructose, galactose, D-glucose, lactose, maltose, mannose, melibiose, and sucrose.

The organisms were tolerant to 0.02 and 0.10% of triphenyltetrazolium chloride.

C. Nutritional Tests

A total of 129 substrates were employed, of which the following 23 substrates were utilized by the organisms as carbon source and energy.

| | |
|---|---|
| D-Xylose | Salicin |
| L-Arabinose | Succinate |
| D-Glucose | Fumarate |
| D-Mannose | L-Malate |
| D-Galactose | DL-Lactate |
| D-Fructose | Pyruvate |
| Sucrose | p-Hydroxybenzoate |
| Trehalose | L-α-Alanine |
| Maltose | DL-Isoleucine |
| Cellobiose | L-Glutamate |
| Lactose | L-Tyrosine |
| Inulin | |

The organisms could not utilize fatty acids, alcohols, and polyalcohols.

D. Antibiotic Susceptibility Tests

The organism was susceptible to carbenicillin, 100 $\mu$g; chlortetracycline, 5 $\mu$g; erythromycin, 15 $\mu$g; gentamicin, 10 $\mu$g; kanamycin, and 30 $\mu$g. The organism was susceptible to the following antibiotics, but resistant colonies appeared. They were colistin, 10 $\mu$g; novobiocin, 30 $\mu$g; polymyxin B, 300 units; and tetracycline, 30 $\mu$g. The organisms were resistant to penicillin, 10 units, and streptomycin, 10 $\mu$g.

E. Identification

The strain S-194 was a Gram-negative, rod shaped bacterium, motile by mixed flagellation, although majority of the cells were polar monotrichously flagellated. The organism was strictly aerobic, and its cytochrome oxidase test was positive. According to Bergey's Manual of Determinative Bacteriology, Buchanan and Gibbons, eds., Williams & Wilkins Company, Baltimore, 8th ed. (1974), such an organism belongs to a member of the genus Alcaligenes, which is currently regarded as an uncertain affiliation. From this standpoint, it is reasonable to conclude that the organism is a member of genus Alcaligenes.

TABLE 2-1

Results of Physiological and Biochemical Tests of Organism S-194

| Test | Results | Test | Results |
|---|---|---|---|
| Cytochrome oxidase | + | Growth at various NaCl concentrations: | |
| Catalase | + | 0.5% (W/V) | + |
| | | 1.5% | + |
| Oxidative and | | 3.0% | − |
| Fermentative | | 6.0% | − |
| (OF) Tests | Oxidative | 7.5% | − |
| | | 10.0% | − |
| Anaerobic growth | − | | |
| Acid production from | | Growth at various pH values: | |
| various carbohydrates: | | pH 4 | − |
| Adonitol | − | pH 6 | + |
| L-Aribinose | + | pH 8 | + |
| Dulcitol | − | pH 10 | − |
| Ethanol | − | pH 12 | − |
| Fructose | + | | |
| Galactose | + | | |
| D-Glucose | + | Indole Test | − |
| Inositol | − | Methyl Red (MR) Test | − |
| Inulin | − | Voges Proskauer (VP) Test | − |
| Lactose | + | Simmons' citrate Test | − |
| Maltose | + | Nitrate reduction | − |
| Mannitol | − | Nitrite reduction | − |
| Mannose | + | Litmus Milk | No change |
| Melibiose | + | | |
| @-Methylglucoside | − | Arginine dihydrolase (ADH) Test | − |
| Raffinose | − | Lysine decarboxylase (LDC) Test | − |
| Rhamnose | − | Ornithine decarboxylase (ODC) Test | − |
| Salicin | − | Ammonia From Peptone | − |
| Sorbitol | − | Phenylaline deaminase (PAD) Test | − |
| Sucrose | + | H$_2$S Production | ± |
| Trehalose | − | Urease Test | − |
| D-Xylose | − | Phosphatase Test | − |
| | | Egg Yolk Test | − |
| Growth in TSI agar: | | | |
| Slant | No Change | Starch hydrolysis | + |
| Butt | No growth | Gelatin hydrolysis | +/± |
| Gas Production | − | Casein hydrolysis | − |
| H$_2$ Production | − | Esculin hydrolysis | + |
| | | Tween 80 hydrolysis | + |
| Growth at various temperatures: | | Pectin hydrolysis | − |
| 4° C. | + | | |

TABLE 2-1-continued

Results of Physiological and Biochemical Tests of Organism S-194

| Test | Results | Test | Results |
|------|---------|------|---------|
| 30° C. | + | 3-Ketolactose production | − |
| 37° C. | + | Congo Red Absorption | − |
| 40° C. | − | | |
| 43° C. | − | Growth with Triphenyltetrazolium | |
| 45° C. | − | Chloride: | |
| 50° C. | − | 0.02% | + |
| | | 0.10% | + |
| Survival at 60° C., 30 min. | − | | |

EXAMPLE 3

UAN 32 Suspension Fertilizer Formulations

A viscous UAN 32 solution containing 0.25% S-194 was prepared using the following formulation:

| | |
|---|---|
| S-194 | 0.25% |
| Water | 22.75 |
| Urea | 36.0 |
| Ammonium Nitrate | 41.0 |

Fertilizers were then prepared from the viscous UAN 32 solution by simply adding dry powders of diammonium phosphate and potassium chloride.

| | N-P-K Analysis | | |
|---|---|---|---|
| Ingredient | 15-10-10 | 14-0-28 | 18-6-12 |
| Viscous UAN 32 | 34.65% | 43.75% | 48.9% |
| Water | 27.5 | 11.1 | 18.7 |
| Diammonium Phosphate | 21.75 | — | 13.05 |
| Potassium Chloride | 16.1 | 45.15 | 19.35 |

A viscous UAN 32 solution containing 0.15% S-194 was prepared using the following formulation:

| | |
|---|---|
| S-194 | 0.15% |
| Water | 22.85 |
| Urea | 36.0 |
| Ammonium Nitrate | 41.0 |

Fertilizers were then prepared from the viscous UAN 32 solutions by simply blending with 10-34-0 polyphosphate and potassium chloride.

| | N-P-K Analysis | | | | |
|---|---|---|---|---|---|
| Ingredient | 10-5-30 | 10-10-20 | 12-8-24 | 15-10-15 | 18-9-9 |
| Viscous UAN 32 | 30.5% | 25.2% | 34.5% | 43.1% | 54.9% |
| Water | 6.4 | 13.1 | 3.2 | 3.3 | 4.1 |
| PAP | 14.7 | 29.4 | 23.6 | 29.4 | 26.5 |
| KCl | 48.4 | 32.3 | 38.7 | 24.2 | 14.5 |

Suspension was fair to good in all formulations and would be improved by air sparging in commercial operations.

EXAMPLE 4

Ammonium Polyphosphate, 10-34-0, Formulations

Suspensions were prepared by first dissolving the S-194 in the available water, followed by the addition of the UAN solution, then the 10-34-0. KCl was added last.

| | N-P-K Analysis | | | | | |
|---|---|---|---|---|---|---|
| Ingredient | 10-5-30 | 10-10-20 | 12-6-24 | 12-12-12 | 15-15-10 | 20-4-8 |
| S-194 | 0.1% | 0.1% | 0.1% | 0.1% | 0.15% | 0.15% |
| Water | 6.3 | 13.0 | 6.9 | 14.9 | 11.15 | 7.85 |
| UAN 28 | 30.5 | 25.2 | 36.6 | 30.3 | 43.1 | 63.3 |
| 10-34-0 | 14.7 | 29.5 | 17.7 | 35.3 | 29.4 | 11.8 |
| KCl | 48.4 | 32.3 | 38.7 | 19.4 | 16.2 | 12.9 |

All of the above formulas produced good suspensions.

EXAMPLE 5

28-28-0 Formulations

Suspensions were prepared by first dissolving the S-194 in the available water, followed by the addition of the UAN solution, then the 28-28-0. KCl was added last.

| | N-P-K Analysis | | | | |
|---|---|---|---|---|---|
| Ingredient | 15-13-13 | 10-10-10 | 15-10-15[1] | 10-10-10[1] | 15-15-15[1] |
| S-194 | 0.1% | 0.1% | 0.1% | 0.1% | 0.1% |
| Water | 23.8 | 42.1 | 22.1 | 32.0 | 22.0 |
| 28-28-0 | 46.4 | 58.6 | 35.7 | 35.7 | 53.6 |
| NH4OH (28% NH3) | 8.7 | 4.3 | — | — | — |
| KCl | 21.0 | 0 | 24.2 | 32.2 | 24.3 |

[1] pH adjusted to 6.5 with concentrated NH4OH

All the above formulas produced good suspensions.

EXAMPLE 6

Flowable Pesticides

To illustrate the shear stability of S-194, 0.25% solutions were sheared in a Dyno-Mill Type KDL-Pilot (Chicago Boiler Co.) wherein glass beads are used as the grinding medium and the high shear is particularly destructive. Viscosities of 4 samples of S-194 are compared with xanthan gum, the most commonly used thickener in flowables.

TABLE 6-1

Gum Shear Stability

| | | Dyno-Mill Shear | |
|---|---|---|---|
| Sample | Initial/Visc.* | 5 min. | 10 min. |
| (1) Xanthan gum | 1300 | 800 | 550 |
| (2) S-194 (1) | 950 | 1160 | 1050 |
| (3) S-194 (2) | 1450 | 3720 | 3920 |
| (4) S-194 (3) | 750 | 2850 | 3150 |
| (5) S-194 (4) | 1200 | 1750 | 1750 |

*Brookfield LVT Visc., Spindle No. 2, 3 rpm.

A flowable sulfur formulation was also prepared according to the following formulation and sheared for five minutes in the Dyno-Mill to illustrate shear stability in a suspension. Low shear rate viscosities were compared with xanthan gum at the same thickener concentration.

| SULFUR FLOWABLE | |
|---|---|
| Sulfur, technical | 52.0% |
| Morwet B ® (sodium n-butyl naphthalene sulfonate, Petrochemicals Co., Inc.) | 1.5 |
| Morwet D-425 ® (Sodium naphthalene formaldehyde condensate) | 2.0 |
| Ethylene Glycol | 5.0 |
| Igepal CO-630 ® (nonylphenoxypoly (ethyleneoxy) ethanol, GAF Corp.) | 1.0 |
| Dow Corning Antifoam A | 0.2 |
| Thickener | 0.16 |
| Water | 38.14 |

Surfactants, dispersants, glycol, and antifoam were dispersed in water followed by the sulfur powder and the thickener. The suspensions were then milled in the Dyno-Mill for five minutes. Viscosities were determined before and after shearing using a Brookfield LVT, spindle No. 3, 3 rpm.

TABLE 6-2

| Pesticide Composition Stability | | |
|---|---|---|
| Thickener | Before milling | After milling |
| Xanthan gum | 4100 cP | 2400 cP |
| S-194 | 2800 cP | 3400 cP |

The suspensions so produced were pourable and stable for three months at ambient temperature and 50° C.

EXAMPLE 7

Viscosity Synergism 0.5% solutions of guar, HP-guar, HEC, and S-194 were prepared. 1:1 Blends of these solutions were also prepared. Viscosities were determined and the data plotted on a graph, from which was determined the expected viscosity. A comparison of the expected vs. observed viscosities indicates that S-194 is synergistic with all three gums.

| | Observed Visc. (cP) | Expected Visc. (cP) |
|---|---|---|
| 0.5% S-194 | 337 | — |
| 0.5% Guar | 112 | — |
| S-194/Guar (50/50) | 395 | 190 |
| 0.5% HP-Guar (Jaquar HP-80) | 295 | — |
| S-194/HP-Guar (50/50) | 520 | 310 |
| 0.5% HEC (Cellosize QP-15M) | 110 | — |
| S-194/HEC (50/50) | 407 | 190 |

What is claimed is:

1. A biologically pure culture of an Alcaligenes microorganism, ATCC 31961.

2. A culture consisting essentially of Alcaligenes microorganism, ATCC 31961, said culture being capable of producing heteropolysaccharide S-194 in recoverable amounts by submerged, aerobic fermentation of an assimilable carbon source.

3. A process for producing heteropolysaccharide S-194 which comprises growing the organism ATCC 31961 in an aqueous nutrient medium by submerged, aerobic fermentation of an assimilable carbon source and recovering said heteropolysaccharide S-194.

4. A process of claim 3 wherein the assimilable carbon is a carbohydrate.

5. A process of claim 3 wherein the carbohydrate is 2%-5% glucose.

6. A process of claim 3 wherein the nutrient medium comprises 3.0% glucose, 0.05% $K_2HPO_4$, 0.2% enzymatic digest of soybean meal, 0.09% $NH_4NO_3$, 0.01% $MgSO_4.7H_2O$, the pH ranges from 6.5 to 7.0, and the temperature of the medium is 30° C.

7. A process of claim 3 wherein the nutrient medium is substantially free of $Ca^{++}$.

* * * * *